United States Patent [19]

Hough et al.

[11] Patent Number: 4,549,013

[45] Date of Patent: Oct. 22, 1985

[54] CHLORO-SUBSTITUTED SUCROSE COMPOUNDS

[75] Inventors: Leslie Hough; Shashikant P. Phadnis, both of London; Riaz A. Khan, Sonning; Michael R. Jenner, Pangbourne, all of England

[73] Assignee: Chemical Bank, New York, N.Y.

[21] Appl. No.: 563,661

[22] Filed: Dec. 20, 1983

Related U.S. Application Data

[62] Division of Ser. No. 755,661, Dec. 30, 1976, Pat. No. 4,435,440.

[30] Foreign Application Priority Data

Jan. 8, 1976 [GB] United Kingdom ............... 616/76
May 12, 1976 [GB] United Kingdom ............ 19570/76

[51] Int. Cl.$^4$ ............................................. C07H 15/24
[52] U.S. Cl. .................................... 536/122; 426/658
[58] Field of Search ........................................ 536/122

[56] References Cited

U.S. PATENT DOCUMENTS

| | | | |
|---|---|---|---|
| 2,684,961 | 7/1954 | Barham | 536/122 |
| 4,296,139 | 10/1981 | Khan et al. | 536/122 |
| 4,335,100 | 6/1982 | Robyt et al. | 536/122 |
| 4,343,934 | 8/1982 | Jenner et al. | 536/122 |
| 4,405,654 | 9/1983 | Lee | 536/122 |

FOREIGN PATENT DOCUMENTS

| | | | |
|---|---|---|---|
| 1543167 | 3/1979 | United Kingdom | 536/122 |
| 2036007 | 4/1980 | United Kingdom | 536/122 |

OTHER PUBLICATIONS

Hough et al., "Chem. Abst.", vol. 84, 1976, p. 31,328(b).
Hough et al., "Chem. Abst.", vol. 84, 1976, p. 105,936(x).

*Primary Examiner*—Johnnie R. Brown
*Attorney, Agent, or Firm*—Ostrolenk, Faber, Gerb & Soffen

[57] ABSTRACT

A method of sweetening a substance comprises incorporating therein a mono- or poly- chloro, mono- or poly-deoxy sucrose derivative having chlorine atoms in selected combinations of positions 4,6,1'- and 6'- of the sucrose molecule. The compounds are many times sweeter than sucrose and are formulated as ingestible products, such as foodstuffs and beverages; oral compositions, such as toothpaste and chewing gum; or sweetening compositions, such as tablets, for addition to beverages, etc.

5 Claims, No Drawings

CHLORO-SUBSTITUTED SUCROSE COMPOUNDS

This is a divisional of U.S. patent application Ser. No. 755,661, filed Dec. 30, 1976, now U.S. Pat. No. 4,435,440.

This invention relates to sweeteners for ingestible products, oral compositions and sweetening compositions.

By an "ingestible product" there is meant one which in the ordinary course of use is intended to be swallowed, for instance a foodstuff or beverage, or an orally administered pharmaceutical composition. By an "oral composition" there is meant one which in the ordinary course of use is not intended to be ingested as such, but is taken into the mouth for the treatment of the throat or buccal cavity, for instance a toothpaste, tooth powder, mouth wash, gargle, troche, dental lotion or chewing gum. By a "sweetening composition" there is meant a composition which is not itself taken orally, either to be ingested or held in the mouth, but instead is intended to be added to other ingestible products or oral compositions to render them sweet or to increase their sweetness.

Although sucrose is still the most widely used sweetening agent, many efforts have been made to find substantially sweeter alternatives which could be used when it is desired to combine a high degree of sweetness with a low calorie content and/or a low risk of dental caries, for example in dietetic products and in the manufacture of soft drinks. The two most successful non-sucrose sweeteners (that is to say sweeteners comprising a compound other than sucrose itself) to data have been saccharin and cyclamate, having respectively about 200 and about 30 times the sweetening powder of sucrose, but the use of these sweeteners, particularly cyclamate, has recently been restricted or banned in some countries because of doubts abou their safety. Saccharin also suffers from the disadvantage of an unpleasantly bitter after-taste which can be detected by many people.

More recently, many other non-sucrose sweeteners have been investigated, some of natural origin and others synthetic, covering a wide range of chemical structures. These compounds have included proteins, such as monellin, thaumatin and miraculin, dipeptides such as aspartame, and dihydrochalcones such as neohesperidin dihydrochalcone. However, apart from the difficulties of synthesizing or extracting such sweeteners, they do not necessarily possess the same quality of sweetness as sucrose: in particular, as compared with sucrose, the sweetness may be slow in onset and relatively lingering, and there may be a liquorice-like or other after-taste, making the sweetener unsuitable as a direct replacement for sucrose unless these differences can be masked.

Although numerous sweeteners of widely diverse chemical structures have now been investigated, it is significant to note that sweetness substantially greater than that of sucrose has not been discovered in any derivative of sucrose or in any other carbohydrate; when an intensely sweet substance has been discovered, such as saccharin, cyclamate and the other non-sucrose sweeteners already mentioned, its structure has always been radically different from that of sucrose. Indeed, it is known tht the presence of some substituents on the sucrose molecule can, in fact, destroy its sweetness and even impart a bitter taste.

Most surprisingly, and in complete contrast to previous knowledge abour non-sucrose sweeteners, we have now discovered that certain derivatives of sucrose and of a sucrose isomer are very much sweeter than sucrose itself, their sweetness being comparable in intensity with that of saccharin, but having a quality similar to that of sucrose.

According to the present invention we provide as sweetening agents sucrose derivatives of the general formula

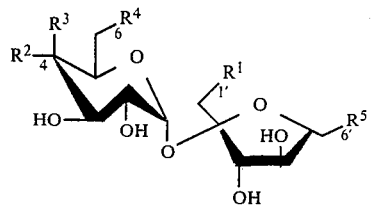

in which $R^1$ represents a hydroxy group or a chlorine atom;

$R^2$ and $R^3$ respectively represent a hydroxy group and a hydrogen atom, a chlorine atom and a hydrogen atom, or a hydrogen atom and a chlorine atom, the 4-position being in the D-configuration;

$R^4$ represents a hydroxy group; or, if at least two of $R^1$, $R^2$, $R^3$ and $R^5$ represent chlorine atoms, $R^4$ represents a hydroxy group or a chlorine atom; and $R^5$ represents a hydroxy group; or, if at least one of $R^1$, $R^2$ and $R^3$ represents a chlorine atom, $R^5$ represents a hydroxy group or a chlorine atom;

provided that at least one of $R^1$, $R^2$, $R^3$ and $R^5$ represents a chlorine atom.

The compounds of formula (I) can be used as sweetening agents in any conventional way, including the sweetening of "ingestible products" (as previously defined), for example foodstuffs, beverages and orally administered pharmaceutical compositions, and of "oral compositions" (as previously defined), for example toothpastes, chewing gums and mouth washes. They can also be used, with conventional liquid or solid extenders and carriers, in "sweetening compositions" (as previously defined).

The extender or carrier comprises any suitable vehicle for the sucrose derivative of the general formula (I) so that it can be formulated in a composition which can conveniently be used for sweetening other products, for example granules, tablets or drops. The extender or carrier may thus include, for example, conventional water-dispersible tabletting ingredients, such as starch, lactose and sucrose itself; low-density bulking agents to provide a granular sweetening composition having a volume per unit sweetness equivalent to that of sucrose, for example, spray dried maltodextrins; and aqueous solutions containing adjuvants such as stabilizing agents, colouring agents and viscosity-adjusting agents.

Beverages, such as soft drinks, containing a sucrose derivative of the general formula (I) may be formulated either as sugar-free dietetic products, or "sugar-reduced" products containing the minimum amount of sugar required by law. In the absence of sugar it is desirable to add further agents to provide a "mouth feel" similar to that provided by sugar, for example pectin or a vegetable gum. For example, pectin may be added at a level of from 0.1 to 0.15% in a bottling syrup.

A number of compounds of the general formula (I) which may be used according to the present invention are shown in the following Table.

TABLE

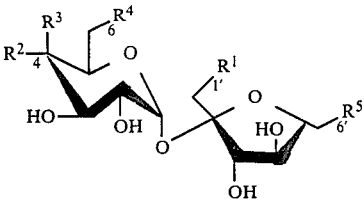

| Compound No. | R$^1$ | R$^2$ | R$^3$ | R$^4$ | R$^5$ | Approximate sweetness (x sucrose)* |
|---|---|---|---|---|---|---|
| 1 | Cl | OH | H | OH | OH | 20 |
| 2 | OH | H | Cl | OH | OH | 5 |
| 3 | Cl | H | Cl | OH | OH | 600 |
| 4 | Cl | OH | H | OH | Cl | 500 |
| 5 | Cl | H | Cl | OH | Cl | 2000 |
| 6 | OH | H | Cl | Cl | Cl | 4 |
| 7 | Cl | OH | H | Cl | Cl | 100 |
| 8 | Cl | H | Cl | Cl | Cl | 200 |
| 9 | Cl | Cl | H | Cl | Cl | 100 |

*Sweetness Evaluation
The sweetness is evaluated in aqueous solution, by comparison with a 10% by weight aqueous solution of sucrose. The results were obtained from a small taste panel and are therefore, not statistically accurate, but indicate the approximate order of sweetness.

The compounds in Table 1 are as follows (the systematic nomenclature is given first, followed by a trivial name based on "galactosucrose" in those cases where a 4-chloro substituent is present):

1. 1'-chloro-1'-deoxysucrose
2. 4-chloro-4-deoxy-α-D-galactopyranosyl-β-D-fructofuranoside [i.e. 4-chloro-4-deoxygalactosucrose]
3. 4-chloro-4-deoxy-α-D-galactopyranosyl-1-chloro-1-deoxy-β-D-fructofuranoside [i.e. 4,1'-dichloro 4,1'-dideoxygalactosucrose]
4. 1',6'-dichloro-1',6'-dideoxysucrose
5. 4-chloro-4-deoxy-α-D-galactopyranosyl-1,6-dichloro-1,6-dideoxy-β-D-fructofuranoside [i.e. 4,1',6'-trichloro-4,1',6'-trideoxygalactosucrose]
6. 4,6-dichloro-4,6-dideoxy-α-D-galactopyranosyl-6-chloro-6-deooxy-β-D-fructofuranoside [i.e. 4,6,6'-trichloro-4,6,6'-trideoxygalactosucrose]
7. 6,1',6'-trichloro-6,1',6'-trideoxysucrose
8. 4,6-dichloro-4,6-dideoxy-α-D-galactopyranosyl-1,6-dichloro-1,6-dideoxy-β-D-fructofuranoside [i.e. 4,6,1',6'-tetrachloro-4,6,1',6'-tetradeoxygalactosucrose]
9. 4,6,1',6'-tetrachloro-4,6,1',6'-tetradeoxysucrose.

From Table 1 it may be seen that chloro substituents at the 4-, 1'- and 6'-positions are effective in inducing sweetness. A combination of two such substituents is synergistic and in general raises the sweetness by approximately one order of magnitude rather than being simply additive. Thus, for example, a 1'-chloro substituent by itself gives a sweetness of 20× and a 4β-chloro substituent by itself a sweetness of 4×. However, a 4,1'-dichloro combination gives a sweetness of 600× and a 1',6'-dichloro combination gives a sweetness of 500×. Similarly, a combination of all three chloro substituents raises the sweetness by approximately one more order, the 4,1',6'-trichloro derivative having a sweeteness of 2000×. (All sweetnesses expressed as multiples of that of sucrose).

In contrast, a 6-chloro substituent is disadvantageous, and causes a reduction in sweetness by antagonising the action of the other substituents. For this reason, a 6-chloro substituent—R$^4$ in formula (I)—may only be present when at least two other chloro substituents are present.

In general, the 6-chloro-substituted compounds are not preferred for this reason—the most sweet compounds containing 4,1'- and 6'-chloro substituents.

The remarkable sweetness of the compounds of formula (I) is combined with an LD$_{50}$ (lethal dose 50%) which, in the case of compound 5 in Table 1, for example, is in excess of 16 g/kg in mice, that being the largest dose which can be administered in practice.

Many of the compounds of the general formula (I) are known and can be prepared by the synthetic routes disclosed in the chemical literature. However, none of the known compounds has previously been recognised as possessing any useful sweetness.

Thus, Compound 5 is reported in Carbohyd. Res., 40, (1975), 285; Compound 6 in Carbohyd. Res., 44, (1975), 37; and Compound 7 in Carbohyd. Res., 25, (1972), 504 and ibid 44, (1975), C12-C13. Compound 2 is reported in Carbohyd. Res., 40, (1975), 285-298.

All of the compounds of the general formula (I), both new and old, may be prepared by reaction of a sucrose ester, having free hydroxy groups in the portions required to be chlorinated, with sulphuryl chloride to obtain the corresponding chlorosulphate derivative. This, on treatment with a source of chloride ions such as lithium chloride, in an amide solvent such as hexamethyl phosphoric triamide, yields the chlorinated sucrose water. Hydrolysis of the chloro-ester, e.g. using sodium methoxide in dry methanol, then liberates the free chlorosucrose. The reaction with sulphuryl chloride is conveniently effected at a reduced temperature in an inert solvent in the presence of a base, for example, chloroform containing pyridine.

A similar method can be used for further chlorinating an already chlorinated sucrose derivative.

In general 4-chloro-sucrose derivatives can be obtained by reaction of the 4-chloro-galactosucrose analogue with a source of chloride ions at an elevated temperature, e.g. 100°-150° C., preferably in the presence of a catalytic amount of iodine.

The following Examples illustrate the invention further (temperatures are given in degrees centigrade).

EXAMPLE 1

1'-chloro-1'-deoxysucrose (Compound 1)

(a) 1'-chloro-1'-deoxysucrose hepta-acetate

A solution of 2,3,4,6,3',4',6'-hepta-O-acetylsucrose (2 g) in a mixture of pyridine (10 ml) and chloroform (30 ml) was treated with sulphuryl chloride (2 ml) at −75° for 45 minutes. The reaction mixture was taken up in ice-cold sulphuric acid (10%, 200 ml) and dichloromethane (200 ml) and shaken vigorously. The organic layer was then successively washed with water, aqueous sodium hydrogen carbonate and water, and then dried (Na$_2$SO$_4$). The solution was concentrated and then extracted with ether. The insoluble material was filtered off and the filtrate concentrated to give the corresponding 1'-chlorosulphate derivative (2.1 g).

This syrupy residue (2 g) was then treated with lithium chloride (2 g) in hexamethyl phosphoric triamide (HMPA) (10 ml) at 90° for 24 hours. The reaction mixture was poured into ice-water, and the precipitate formed was collected, washed with water, and taken up in ether. The organic layer was dried over sodium sulphate, concentrated and eluted from a silica gel column with ether—light petroleum (1:1) to give the 1'-chloro hepta-acetate as an amorphous powder $[\alpha]_D +55.0°$ (c 1.2, CHCl$_3$); n.m.r. data: $\tau$ 4.29 (d, $J_{1,2}$ 3.5 Hz, H-1); 5.11 (dd, $J_{2,3}$ 10.0 Hz, H-2); 4.56 (t, $J_{3,4}$ 9.5 Hz, H-3); 4.94 (t, $J_{4,5}$ 9.5 Hz, H-4); 4.32 (d, $J_{3',4'}$ 6.5 Hz, H-3'); 4.60 (t, $J_{4',5'}$ 6.5 Hz, H-4'); 7.84–8.01 (7 Ac). Mass spectral data: [(a) indicates ions due to hexapyranosyl cation and (b) a 3:1 doublet (1Cl) due to ketofuranosyl]: m/e 331 a, 307 b, 187 b, 169 a, 145 b, 109 a.

Analysis calculated for C$_{26}$H$_{35}$ClO$_{17}$: C,47.7; H,5.4; Cl,5.4%; Found: C,47.5; H,5.6; Cl,5.7%.

(b) 1'-chloro-1'-deoxysucrose

A solution of the above intermediate (1 g) in dry methanol (10 ml) was treated with a catalytic amount of M sodium methoxide in methanol at room temperature for 5 hours. T.l.c. (dichloromethane-methanol, 3:1) showed a slow-moving product. The solution was de-ionized by shaking with Amberlyst −15 (a polystyrene sulphonic acid resin), in H$^+$ form, concentrated, and purified by shaking an aqueous solution of the syrup with petrol. The aqueous layer was then concentrated and dried under vacuum to give 1'-chloro-1'-deoxysucrose $[\alpha]_D +57.8°$ (c 0.7, water).

Analysis calculated for C$_{12}$H$_{21}$ClO$_{10}$: C, 39.9; H, 5.9; Cl, 9.8%; Found: C, 39.7; H, 6.1; Cl, 9.7%.

EXAMPLE 2

4,1'-dichloro-4,1'-dideoxygalactosucrose (Compound 3)

(a)
2,3,6-Tri-O-acetyl-4-chloro-4-deoxy-α-D-galactopyranosyl-3,4-di-O-acetyl-6-O-benzoyl-1-chloro-1-deoxysucrose A solution of 2,3,6,3',4'-penta-O-acetyl-6'-O-benzoylsucrose (2 g) in a mixture of pyridine (10 ml) and chloroform (30 ml) was treated with sulphuryl chloride (2 ml) at −75° for 45 minutes. The reaction mixture was poured into ice-cold sulphuric acid (10%, 200 ml) with vigorous shaking and then extracted with dichloromethane. The organic layer was washed successively with water, aqueous sodium hydrogen carbonate, and water, and dried (Na$_2$SO$_4$). The solution was concentrated and extracted with ether. The insoluble material was filtered off and the filtrate concentrated to give the chlorosulphate (2.1 g). This intermediate was then treated with lithium chloride as in Example 1 to give the above-named chloro intermediate.

(b)
4-chloro-4-deoxy-α-D-galactopyranosyl-1-chloro-1-deoxy-β-D-fructofuranoside

A solution of the above intermediate from (a) (1 g) in dry methanol was treated with a catalytic amount of M sodium methoxide in methanol at room temperature for 5 hours. T.l.c. (dichloromethane-methanol, 4:1) showed one product. The reaction was worked up as described in Example 1(b) to give the title product as a syrup, $[\alpha]_D +49.6°$ (c 0.7, water).

Analysis calculated for C$_{12}$H$_{20}$Cl$_2$O$_9$: C,38.0; H, 5.3; Cl, 18.7%; Found: C, 35.7; H, 6.0; Cl, 20.4%.

By a similar method 1',6'-dichloro-1',6'-dideoxysucrose (Compound 4) was prepared: $[\alpha]_D +67°$(c 1.0, methanol).

Analysis calculated for C$_{12}$H$_{20}$Cl$_2$O$_9$: C, 38.0, H; 5.3; Cl, 18.7%; Found: C, 37.7; H, 5.2; Cl, 17.1%.

Hexa-acetate—white solid foam, $[\alpha]_D +51.7°$(c 1.0, CHCl$_3$) Mass spectrometry m/e 331 and 283 (2 Cl).

Characterized by reductive dehalogenation with Raney Nickel, H$_2$ and KOH to 1',6'-dideoxysucrose hexaacetate—a thick colourless syrup; $[\alpha]_D +25.5°$(c 1.0, CHCl$_3$). 100 Hz N.M.R. (C$_6$D$_6\tau$ values)—H-1, 4.36 d ($J_{1,2}$ 3.5 Hz); H-2, 4.99 q ($J_{2,3}$ 10.5 Hz); H-3, 4.17 t ($J_{3,4}$ 10.0 Hz); H-4, 4.71 t ($J_{4,5}$ 10.0 Hz); H-1', 8.58 s; H-6', 8.60 d.

EXAMPLE 3

1,6-dichloro-1,6-dideoxy-β-D-fructofuranosyl-4,6-dichloro-4,6-dideoxy-α-D-galactopyranoside (Compound 8)

A solution of 6,1',6'-trichloro-6,1',6'-trideoxysucrose (3 g) in pyridine (70 ml) was treated with sulphuryl chloride (35 ml) in dry chloroform (100 ml) at −75° for 3 hours. The solution was stirred at 0° to <5° for 2 hours and then at room temperature for 24 hours. The reaction mixture was then diluted with dichloromethane (100 ml) and washed successively with ice-cold sulphuric acid (10%, 250 ml), water, aqueous sodium hydrogen carbonate, and water. The organic layer was dried over sodium sulphate and concentrated to give a syrup. The syrupy residue was dissolved in methanol (100 ml) and dechlorosulphated by means of excess barium carbonate and a catalytic amount of sodium iodide. The inorganic residue was filtered off and the filtrate concentrated to a syrup. T.l.c. (chloroform—methanol, 4:1) showed the 4,6,1',6'-tetrachloro-4,6,1',6'-tetradeoxygalactosucrose as the major product. A fast-moving minor product, probably a pentachloro derivative, was also observed. Purification on a column of silica gel, using chloroform—acetone (5:1) gave the tetrachloro derivative in 90% yield.

Precisely equivalent results were obtained by repeating the above procedure but starting from 1',6'-dichloro-1',6'-dideoxysucrose or 1'-chloro-1'-deoxysucrose, instead of the 6,1',6'-trichloro-6,1',6'-trideoxysucrose.

$[\alpha]_D +89°$(c 1.0, methanol). Mass spectroscopy: m/e 199 (2-Cl).

Tetra-acetate—white solid foam, $[\alpha]_D +98.5°$(c 1.0, CHCl$_3$). 100 MHz N.M.R. (CDCl$_3$, $\tau$ values)—4.28 d (H-1), 5.25 q (H-4), 4.30 d (H-3'), 4.55 t (H-4')$J_{1,2}$ 3.5 Hz; $J_{3,4}$ 3.0 Hz; $J_{4,5}$ 1.5 Hz; $J_{3',4'}$ 6.5 Hz; $J_{4',5'}$ 6.5 Hz. Mass spectrometry m/e 283 (2 Cl).

Tetra-mesylate—very pale yellow crystals from dichloromethane—ethanol; m.p. 120°–121°; $[\alpha]_D +65.5°$(c 1.0, CHCl$_3$). 100 MHz N.M.R. (CDCl$_3$, $\tau$ values) H-1 4.18 d ($J_{1,2}$3.5 Hz); H-2 5.06 q ($J_{2,3}$ 10 Hz); H-3 4.77 q ($J_{3,4}$ 3.5 Hz); H-4 5.20 q ($J_{4,5}$ 1.5 Hz); H-3' 4.39 d ($J_{3',4'}$ 7.0 Hz); H-4' 4.65 t ($J_{4',5'}$ 7.0 Hz); Mass spectrometry m/e 355 (2 Cl).

EXAMPLE 4

4,6,1',6'-tetrachlorosucrose (Compound 9)

To a solution of 4,6,6'-trichloro-4,6,6'-trideoxy-2,3,3',4'-tetra-O-acetylgalactosucrose 1'-O-monomesitylenesulphonate (1 g) in D.M.F. (15 ml) was added excess of lithium chloride (2 g) and a catalytic amount of iodine (50 mg) and the mixture was heated at 140°–145° in an oil-bath for 18 hours. T.l.c. (benzene—ethylacetate 3:1) indicated the presence of a major product moving faster than the starting material. The reaction mixture was cooled, poured into ice-cold water and then extracted with ethyl acetate. The organic extract was washed thoroughly, first with 5% sodium thiosulphate solution and then with water, and dried. The ethyl acetate was evaporated off and the residue was treated with methanol containing a catalytic amount of sodium methoxide.

T.l.c. (chloroform/acetone/methanol/water, 57:20:20:3) now showed the presence of a faster-moving minor product and a slower-moving major product—both having very similar mobilities and the latter corresponding to 4,6,1',6'-tetradeoxy-galactosucrose (Compound 8) (mixed t.l.c.). The mixture was fractionated over a column of silica gel using chloroform-methanol (10:1) as eluent. Although complete separation was not achieved because of the close mobilities of the two components, the first few fractions contained 4,6,1',6'-tetrachloro-4,6,1',6'-tetradeoxy-sucrose which was obtained as a white solid $[\alpha]_D+45°$(c 1.0, MeOH). The structure was confirmed by n.m.r. and mass spectrometry of the following derivatives:

Tetraacetate—syrup, $[\alpha]_D+30.5°$(c 1.0 CHCl$_3$) N.M.R. (C$_6$D$_6$ $\tau$ values)—H-1, 4.39 d (J$_{1,2}$ 4.35 Hz); H-2,5.14 q (J$_{2,3}$ 10 Hz); H-3, 4.27 t (J$_{3,4}$ 10 Hz); H-4, 6.1 t (J$_{4,5}$ 10 Hz); H-3', 4.20 d (J$_{3',4'}$ 9.6 Hz); H-4', 4.62 t (J$_{4',5'}$ 6.0 Hz).

Tetra-mesylate—white crystalline compound m.p. 187° (dichloromethane—methanol) $[\alpha]_D+29.9°$(c 1.0, acetone).

EXAMPLE 5

Sweetening tablets for beverages, etc.

| Each tablet contains: | |
|---|---|
| Compound 3 | 8 mg |
| or Compound 5 | 2 mg | together with a dispersable tablet base (ca. 60 mg) containing sucrose, gum arabic and magnesium stearate, and is equivalent in sweetness to about 4.5 g sucrose.

EXAMPLE 6

Bulked sweetener

A bulked sweetener having the same sweetness as an equivalent volume of sucrose (granulated sugar) is prepared by mixing the following ingredients and spray-drying to a bulk density of 0.2 g/cc:

| maltodextrin solution containing dry weight | 222.2 g |
|---|---|
| Compound 3 | 1.7 g |
| (or Compound 5 | 0.5 g). |

The resulting composition has a sweetening power equivalent to approximately 2 kilograms of sugar.

EXAMPLE 7

Reduced calorie cola drink containing sugar

| Ingredients to prepare 100 ml bottling syrup: | |
|---|---|
| Compound 3 | 80 mg |
| (or Compound 5 | 20 mg) |
| Sugar | 60 g |
| Benzoic acid | 35 mg |
| Phosphoric acid (conc.) | 1 ml |
| Cola flavour | 1.1 ml |
| Colour | ad-lib. |

Make up to 100 ml with mineral water. This syrup may then be added in 25 ml doses to carbonated 225 ml aliquots of chilled mineral water.

EXAMPLE 8

Carbonated low calorie lemonade (sugar-free)
Ingredients to prepare 100 ml syrup:

| Compound 3 | 100 mg |
|---|---|
| (or Compound 5 | 19 mg) |
| Benzoic acid | 35 mg |
| Citric acid (dry base) | 1.67 g |
| Lemon essence | 0.8 g |

Make up to 100 ml in mineral water. This syrup can be added in 25 ml doses to 225 ml aliquots of carbonated chilled mineral water.

EXAMPLE 9

Toothpaste

| | % by weight |
|---|---|
| Dibasic calcium phosphate | 50% |
| Glycerol | 20% |
| Sodium lauryl sulphate | 2.5% |
| Spearmint oil | 2.5% |
| Gum tragacanth | 1.0% |
| Compound 3 | 0.03% |
| Water | 23.97% |

The ingredients are mixed to produce a spearmint flavoured toothpaste of acceptable sweetness but free from sugar or saccharin.

EXAMPLE 10

Chewing Gum

| | part by weight |
|---|---|
| Polyvinyl acetate | 20 |
| Butyl phthalylbutylglycolate | 3 |
| Polyisobutylene | 3 |
| Microcrystalline wax | 2 |
| Calcium carbonate | 2 |
| Flavouring/aroma | 1 |
| Compound 3 | 0.07 |
| Glucose | 10 |

The above chewing gum base can be cut into conventional tablets or strips.

The 1',6'-dichloro derivative can be prepared by reacting sucrose with mesitylenesulphonyl chloride, separating the desired dimesitylene sulphonates from the mixture of substituted sucroses by, for example, chromatography and replacing the mesitylenesulphonyloxy substituents with chlorine atoms by reaction with lithium chloride after protecting the remaining free hydroxyl groups by esterification, for example, with acetic anhydride.

From the above noted mixtures of mesitylenesulphonate substituted sucroses, the 6,1',6' trisubstituted sucrose derivate, which is present in relatively large proportions, can be separated. This tri-substituted derivative can, in a manner similar to that noted above, be converted to the 6,1',6'-trichloro-substituted derivative. From this trichloro-substituted derivative, the desired tetrachloro-substituted derivative can be prepared in good yields, after de-esterification followed by reaction with sulphuryl chloride at low temperatures.

Other potential ways of preparing the 1',6'-dichlorosucrose derivatives of the invention include chlorinating the 4,6-benzylidene derivatives of sucrose, while other potential ways of preparing the 4,6,1',6'-tetrachlorosucrose derivatives include reacting sucrose with mesitylenesulphonyl chloride under more severe conditions to promote the formation of the tetra-substituted derivative followed by replacing the four mesitylenesulphonyloxy substituents with chlorine atoms.

The preparation of the chloro-derivatives of sucrose by these methods will now be illustrated by the following Examples.

EXAMPLE 11

Sucrose was treated with mesitylenesulphonyl chloride (3 mole) in pyridine at −5° C. for 6 days to give a major product 1',6,6'-tri-O-mesitylenesulphonylsucrose as described by L. Hough, S. P. Phadnis and E. Tarelli, Carbohydrate Research, 1975, 44, C 12 and C 13 to which reference is directed. Thus, concentration of the reaction mixture and conventional extraction of the residue into chloroform gave 6-O-mesitylenesulphonyl-α-D-glucopyranosyl-1,6-di-O-mesitylenesulphonyl-β-D-fructofuranoside (melting point 135° C. [dec]). More of this compound was obtained from the mother liquors after chromatography on silica gel. This compound was then converted into 6-chloro-6-deoxy-α-D-glucopyransoyl-1,6-dichloro-1,6-dideoxy-62-D-fructofuranoside by treatment of the penta-acetate with lithium chloride in N,N-dimethylformamide containing a trace of iodine at 140° C. for 18 hours (melting point 127° C. from ethanol, $[\alpha]_D +58°$; c 1 chloroform).

EXAMPLE 12

The mother liquors from the concentration and extraction step of Example 11 were subjected to chromatography on silica gel to give a mixture of isomeric disulphonate. Upon the addition of 2-propanol or ethanol, the 1',6'-dimesitylenesulphonate crystallized and was identified [melting point 129° to 130° C.; $[\alpha]_D +67.5°$ (methanol)].

The dimesitylenesulphonate was acetylated by treatment with acetic anhydride and then reacted at 140° C. for 18 hours with lithium chloride in N,N-dimethylformamide containing a trace of iodine to give the 1',6'-dichloride in a high yield. This dichloride was characterized by $^1$H-n.m.r., mass spectrometry and by conversion to the corresponding 1',6'-dideoxy compound.

EXAMPLE 13

The 6,1'-6'-tri-O-mesitylenesulphonylsucrose prepared in Example 11 was acetylated by treatment with acetic anhydride and reacted at 140° C. for 18 hours with lithium chloride in N,N-dimethylformamide containing a trade of iodine to give the 6,1',6'-trichloride.

This trichloride was then de-O-acetylated by treatment with methanolic sodium methoxide and the product (1 mole) was dissolved in pyridine, cooled to −40° C. and a solution of sulphuryl chloride (10 mole) in chloroform was added dropwise. The reaction mixture was allowed to warm to 0° C., kept at this temperature for 24 hours, after which it was poured into ice-cold, 10% sulphuric acid. The mixture was extracted with chloroform, the extract washed with aqueous sodium bicarbonate, then water and dried with MgSO$_4$. Evaporation of the chloroform, followed by de-chlorosulphation in methanol using sodium iodide and sodium carbonate as described by L. Hough, S. P. Phadnis and E. Tarelli in Carbohydrate Research, 1975, 44, 37–44, gave the crude 4,6,1',6'-tetrachlorogalactosucrose. This was then purified by conversion to the tetra-O-acetate, followed by column chromatography and de-O-acetylation.

The desired tetrachloro compound was characterized by $^{13}$C-n.m.r., mass spectrometry and by conversion into the tetramethanesulphonate [melting point 120°–121° C.; $[\alpha]_D +65.5°$(c 1 chloroform)].

We claim:
1. 1'-chloro-1'-deoxysucrose.
2. 4-chloro-4-deoxy-α-D-galactopyranosyl-1-chloro-1-deoxy-β-D-fructofuranoside.
3. 4,6,1',6'-tetrachloro-4,6,1',6'-tetradeoxysucrose.
4. 1',6'-dichloro-1',6'-dideoxysucrose.
5. 4,6,-dichloro-4,6,-dideoxy-α-D-galactopyranosyl-1,6,-dichloro-1,6-dideoxy-β-D-fructofuranoside.

* * * * *